(12) United States Patent
Greenhalgh

(10) Patent No.: US 6,364,895 B1
(45) Date of Patent: Apr. 2, 2002

(54) INTRALUMINAL FILTER

(75) Inventor: E. Skott Greenhalgh, Wyndmoor, PA (US)

(73) Assignee: Prodesco, Inc., Perkasie, PA (US)

(*) Notice: Subject to any disclaimer, the term of this patent is extended or adjusted under 35 U.S.C. 154(b) by 0 days.

(21) Appl. No.: 09/494,323

(22) Filed: Jan. 28, 2000

Related U.S. Application Data

(60) Provisional application No. 60/158,197, filed on Oct. 7, 1999.

(51) Int. Cl.$^7$ .............................................. A61M 29/00
(52) U.S. Cl. ....................................................... 606/200
(58) Field of Search ................................ 606/200, 127, 606/159, 113, 114, 128, 108

(56) References Cited

U.S. PATENT DOCUMENTS

| | | | | |
|---|---|---|---|---|
| 4,425,908 A | * | 1/1984 | Simon | 606/200 |
| 5,108,418 A | * | 4/1992 | Lefebvre | 606/200 |
| 5,397,331 A | | 3/1995 | Himpens et al. | 606/151 |
| 5,718,159 A | | 2/1998 | Thompson | 87/33 |
| 5,814,064 A | * | 9/1998 | Daneil et al. | 606/200 |
| 5,925,060 A | | 7/1999 | Forber | 606/191 |
| 5,954,745 A | | 9/1999 | Gertler et al. | 606/200 |
| 6,027,520 A | | 2/2000 | Tsugita et al. | 606/200 |
| 6,059,814 A | | 5/2000 | Ladd | 606/200 |

* cited by examiner

*Primary Examiner*—Kevin Truong
(74) *Attorney, Agent, or Firm*—Synnestvedt & Lechner LLP

(57) ABSTRACT

An intraluminal filter for vascular use during medical procedures is disclosed. The filter is formed of a plurality of flexible, resilient monofilament wires interbraided in a relatively open mesh forming a basket with a plurality of multifilament yarns braided in a relatively closed mesh having a predetermined porosity forming a filter element. The filter element is positioned distally of the basket forming a concave portion, the remaining portion of the basket being unobstructed and forming openings facing the concave portion. The filter is elastically deformable between two shape states, the first having a small diameter enabling the filter to slide within the bore of a catheter for positioning the filter in the lumen of an artery, the second shape state having a substantially larger diameter sized to sealingly interfit within the artery lumen. The filter is biased and will expand upon release from the catheter to the second shape state. The open portion is positioned upstream allowing blood to flow into the concave portion of the filter element, particles above a certain size being captured in the filter while blood is allowed to flow through. A tether is attached to the upstream end of the filter allowing it to be withdrawn into the catheter bore for removing the filter from the artery.

23 Claims, 6 Drawing Sheets

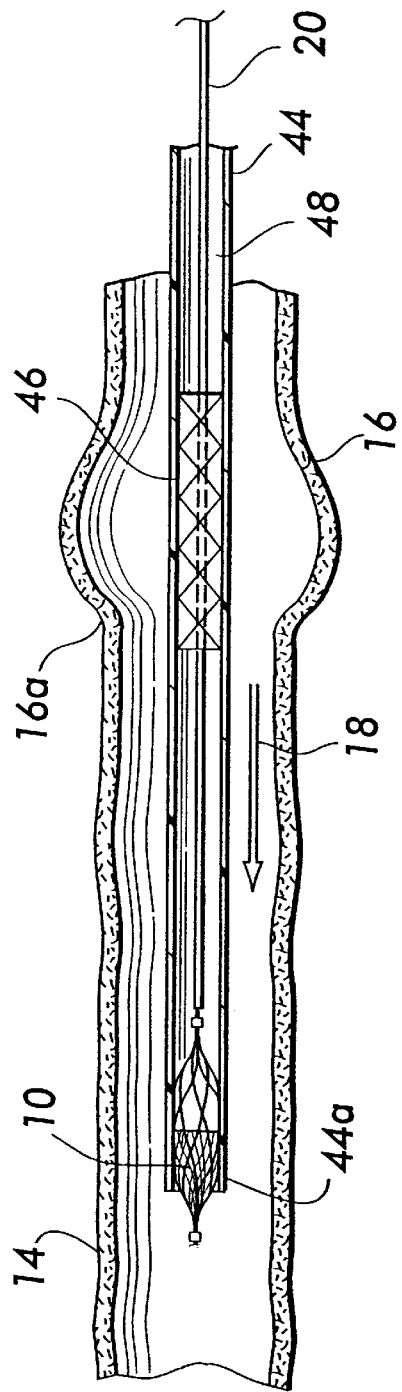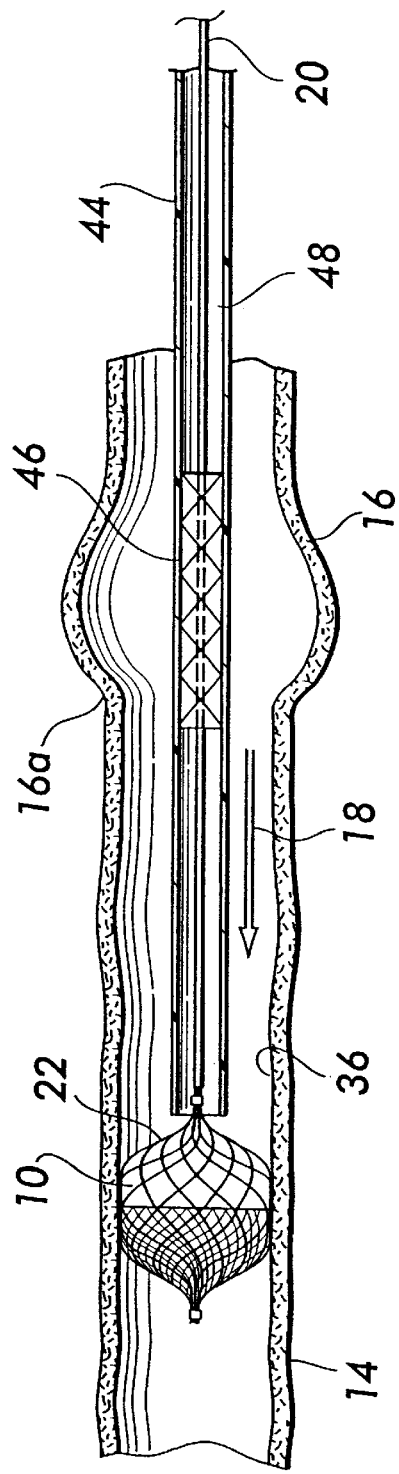

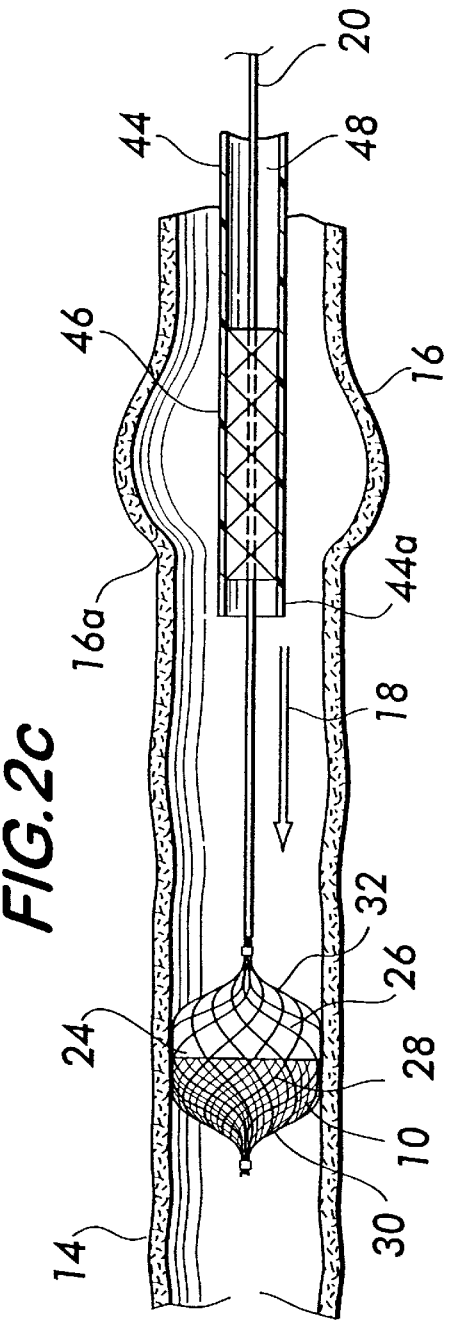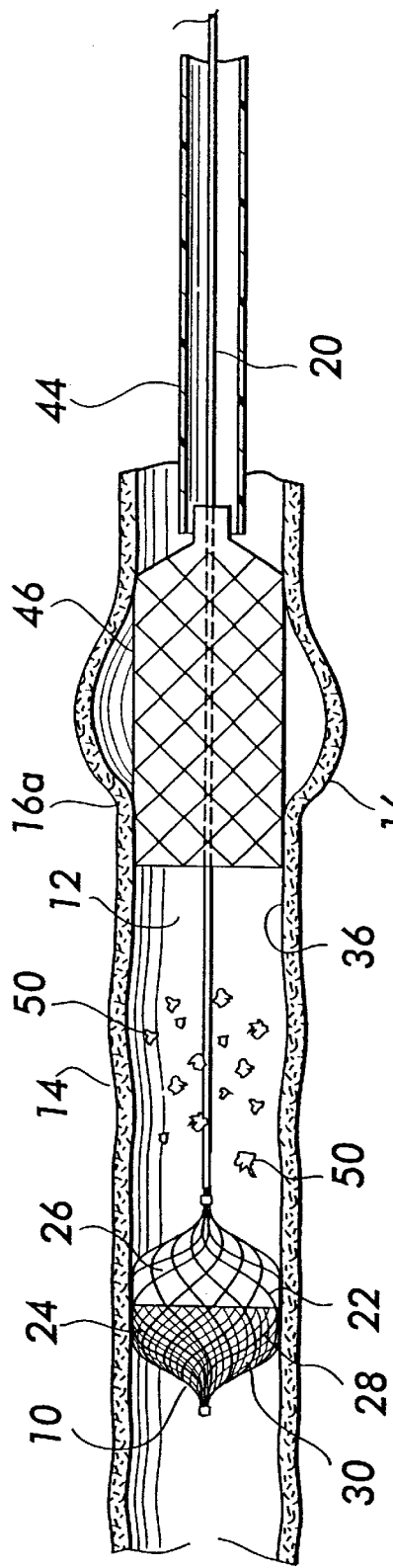

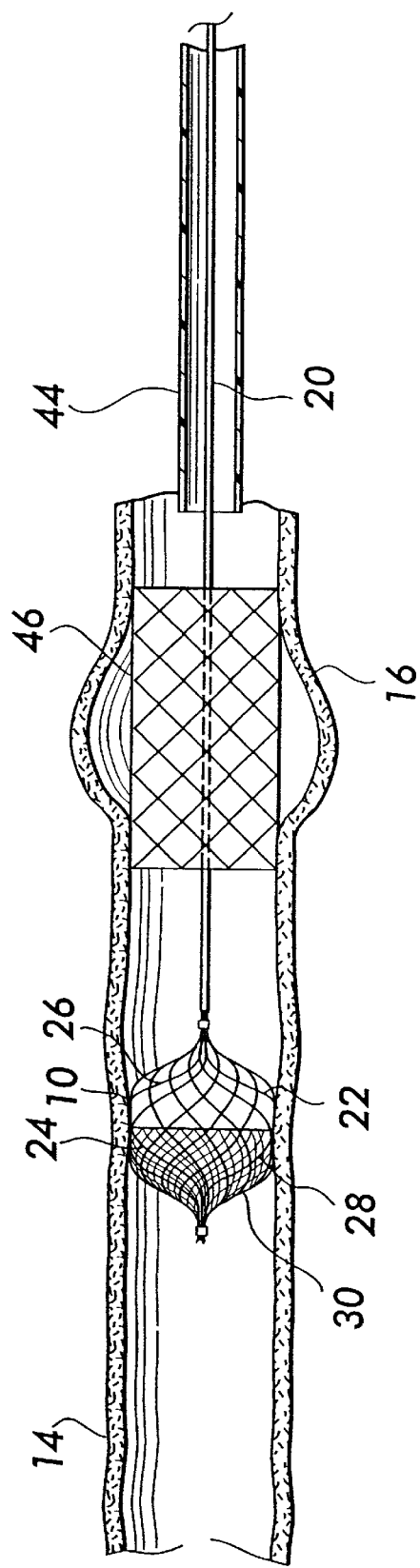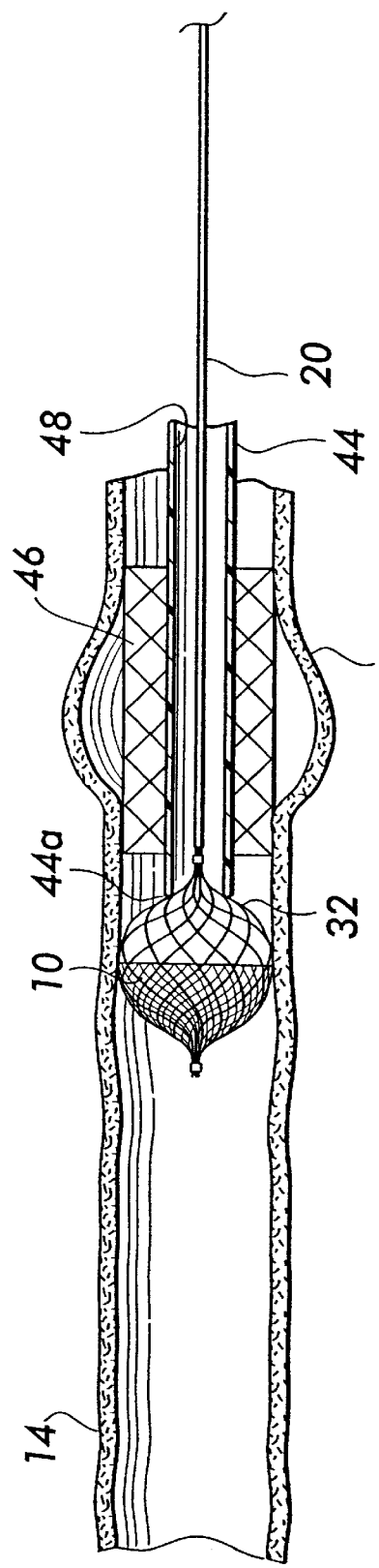

INTRALUMINAL FILTER

RELATED APPLICATIONS

This application is based on and claims the benefit of prior filed co-pending provisional patent application Ser. No. 60/158,197, filed Oct. 7, 1999.

FIELD OF THE INVENTION

This invention relates to a filter temporarily positionable in a lumen, for example, the lumen of an artery, for trapping and removing particles from a fluid flowing through the lumen while allowing the fluid to flow relatively unimpeded through it.

BACKGROUND OF THE INVENTION

Various vascular procedures, such as the removal of a stenosis occluding an artery or the positioning of a stent graft to reinforce the weakened artery wall at an aneurysm, tend to dislodge particles or emboli from the wall of the artery. The dislodged emboli become entrained in the blood stream flowing through the lumen of the artery. If allowed to remain in the blood flow, the emboli are carried through the vascular system until they lodge in a blood vessel thereby forming a blockage or embolism. Depending upon the size and/or volume of the emboli and where in the vascular system they lodge, the consequences of an embolism can be extremely serious, resulting, for example, in the sudden cessation of blood flow to an extremity, an organ, such as a kidney, the brain or the heart.

There is clearly a need for a filter which can be temporarily positioned in the lumen of an artery downstream from the point where a medical procedure is taking place which may dislodge emboli from the artery wall. The filter should trap emboli above a predetermined size but allow the blood to flow through relatively unimpeded. The filter should be removable from the artery after the procedure is complete and no further emboli are dislodged, the filter bringing all of the trapped emboli with it out of the vascular system.

SUMMARY AND OBJECTS OF THE INVENTION

The invention concerns an intraluminal filter positionable within a lumen for separating particles from a fluid flowing within the lumen. Although other applications are envisioned, the filter is particularly well suited for vascular use.

In its preferred embodiment, the intraluminal filter according to the invention comprises a first plurality of filamentary members interlaced in a relatively open mesh to form a basket and a second plurality of filamentary members interlaced with one another and with the first filamentary members to form a concave first portion of the basket which is distally positioned and acts as a filter as described below. A second portion of the basket, arranged to face the concave first portion, remains substantially unobstructed and forms openings according to the density of the filamentary members as determined by their size and number, the openings being sized to allow both the fluid and the particles to flow into the concave first portion when the second portion of the basket is oriented upstream within the lumen.

The surface formed by the second filamentary members comprises a filter element having openings of predetermined size smaller than the first named openings in the first portion. The second openings are sized to capture the particles entrained within the fluid while allowing the fluid to flow through the surface.

Preferably, the first filamentary members are formed of a flexible resilient material, such as monofilament wires of the shape memory alloy nitinol. Due to their flexible resilience, the first filamentary members allow the basket to deform elastically from a first shape state to a second shape state. The first shape state has a first diameter sized to allow the basket to slidingly fit within the bore of a catheter positionable within the lumen. The catheter provides the preferred means for positioning the intraluminal filter within the lumen, especially a vascular lumen.

The second shape state has a second diameter substantially larger than the first diameter. The second diameter is sized to allow the basket to sealingly interfit within the lumen and present the filter element substantially across the direction of fluid flow. The basket is biased by internal elastic forces within the first filamentary members to assume the second shape state when released from the catheter.

Preferably, the first filamentary members are interlaced by braiding, a method of interlacing which allows the basket to readily assume the first and second shape states. It is convenient to form the basket by braiding the first filamentary members into a tube having a predetermined length. The tube has oppositely arranged ends which are gathered and cinched to form the basket. Preferably, one of the ends forms the second portion of the basket which is not obstructed by the second filamentary members, thus, forming the first openings at that end.

The second filamentary members are preferably multifilament polyester yarns which allows them to be readily heat sealed to the first filamentary members adjacent to the second portion of the basket. The yarns are also interlaced by braiding with one another and further interlaced with the first filamentary members to secure the filter element formed by the yarns to the basket. The yarns are braided in a relatively closed mesh to form the filter means. The characteristics of the braiding are used to control the porosity of the filter means by tailoring the size of the openings in the filter to capture particles above a predetermined size but allow particles below that size to pass. Thus, emboli in a vascular lumen caused by a surgical procedure can be captured by the filter while components of blood, such as the corpuscles and plasma, will not be significantly impeded.

In an alternate embodiment, the filter includes a plurality of projecting members having end portions projecting angularly outwardly. The end portions are interengagable with the lumen and prevent downstream movement of the filter. The end portions are arranged to point in the downstream direction to allow them to readily disengage from the lumen when the filter is moved in an upstream direction for retraction of the filter into the catheter.

The end portions can be conveniently formed by cutting the selected filaments forming the basket at points adjacent to the concave first portion of the basket. The end portions adjacent to the first portion of the basket are relatively unrestrained by the relatively open mesh of the first filamentary members which allow the ends to project angularly outwardly. The complementary end portions at the second portion of the basket which result from the cut filaments are restrained by the second filamentary members forming the filter element and, thus, do not tend to extend outwardly from the filter. Preferably, the cut filaments forming the projecting members are present in a one to one ratio with the uncut filaments forming the basket.

It is advantageous to attach a flexible tether to the unobstructed end of the basket. The tether has a predetermined length and is extendable through the catheter for allowing the intraluminal filter to be manually withdrawn from the lumen into a catheter bore, for example, after completion of a surgical procedure when the filter is no longer required. The filter, along with the captured emboli, are then removed from the lumen when the catheter is removed.

A preferred method of forming an intraluminal filter according to the invention comprises the steps of:

(a) braiding a plurality of flexible, resilient filamentary members into a relatively open mesh forming an elastically deformable tube, the filamentary members providing a radial bias to the tube, urging the tube to assume a predetermined length and diameter;

(b) interbraiding a multiplicity of yarns with the first filamentary members to form, with the filamentary members, a surface having a predetermined porosity, the surface comprising the filter element or means;

(c) gathering each end of the tube and cinching each end together to form an elastically deformable basket;

(d) removing the yarns from a portion of the basket at one end of the tube, thereby forming openings at the one end which allow the fluid and particles to flow into the filter; and (e) attaching the yarns to the first filamentary members adjacent to the unobstructed portion of the basket.

Although the steps of removing and attaching the yarns can be accomplished in any of several ways, it is preferred to use a laser to ablate the multifilament yarns from the portion of the basket which is to be unobstructed and use the same laser to heat seal the yarns to the filamentary members adjacent to the unobstructed portion of the basket. The laser allows for pinpoint accuracy in targeting the yarns to be removed and heat sealed.

It is an object of the invention to provide a filter positionable within the lumen of an artery.

It is another object of the invention to provide a filter having a filter element of braided filamentary members to capture emboli above a certain size entrained with the blood in the artery.

It is yet another object of the invention to provide a filter which is elastically collapsible into a first shape state having a diameter sized to permit the filter to slidingly interfit within a catheter bore for positioning the filter within the artery lumen.

It is still another object of the invention to provide a filter which is self-expanding into a second shape state having a second diameter substantially larger than the diameter of the first shape state, the second diameter being sized to allow the filter to sealingly interfit within the artery lumen.

It is again another object of the invention to provide a filter which is collapsible from the second shape state to the first shape state by withdrawing the filter into the catheter bore for removing the filter from the artery lumen.

These and other objects will become apparent from a consideration of the following drawings and detailed description of the invention.

BRIEF DESCRIPTION OF THE DRAWINGS

FIGS. 2a–2f are partial cross-sectional views depicting a sequence of steps for deploying and recovering an intraluminal filter to and from an artery as seen in FIG. 1;

DETAILED DESCRIPTION OF THE PREFERRED EMBODIMENT

The intraluminal filter for vascular use preferably comprises a flexible, resilient structure adapted to assume at least two different shape states, the first shape state being adapted to interfit slidably within the lumen of an insertion catheter, the second shape state being adapted to interfit within the lumen of a vascular vessel. The resilient structure further comprises a distally arranged filter element which sealingly engages the inside circumference of the vessel to trap and retain emboli flowing through the vessel, the emboli being removed from the vascular system upon withdrawal of the intraluminal filter.

Figure 1:
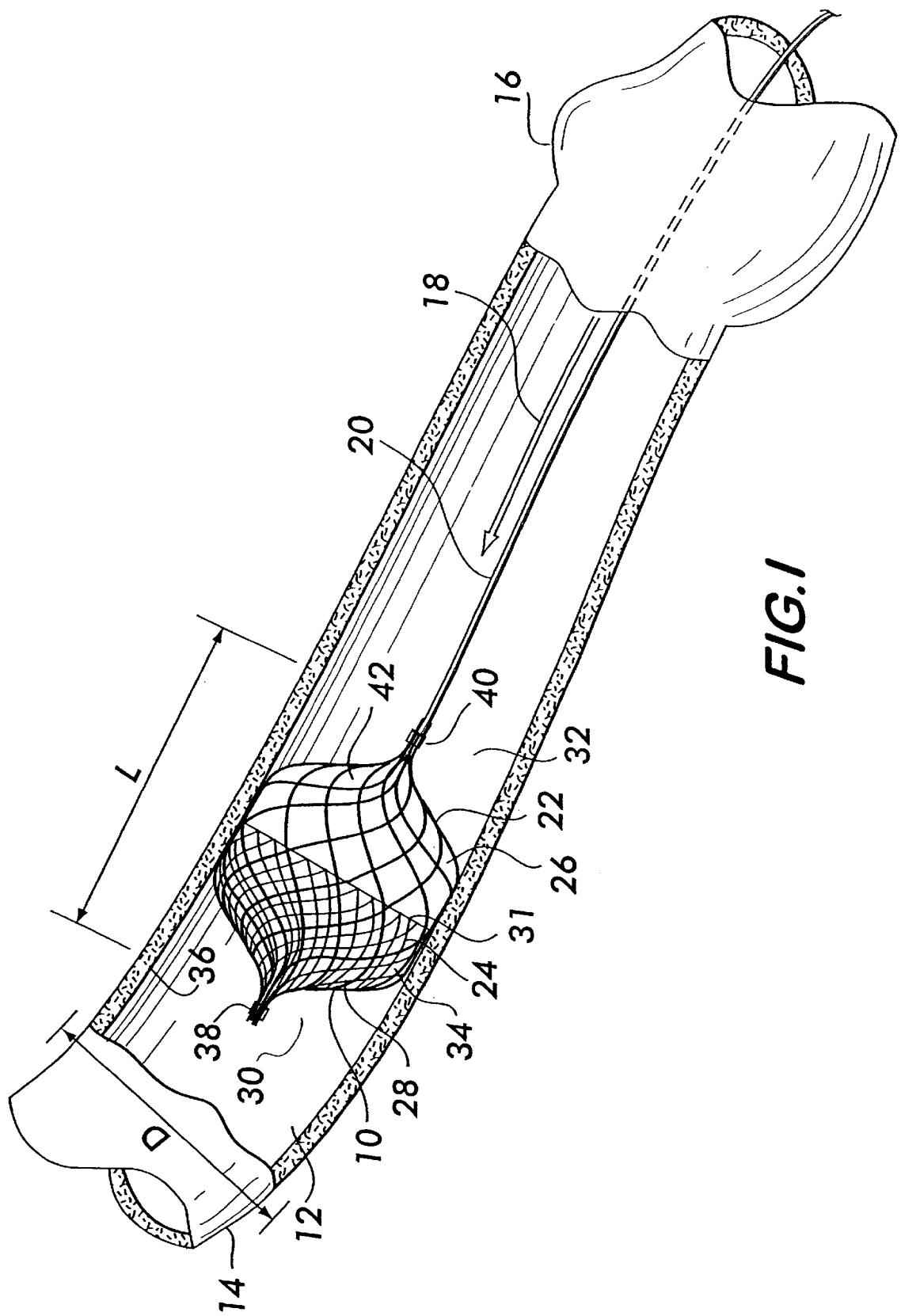
FIG. 1 is a partial cross-sectional view of an intraluminal filter according to the invention positioned in an artery.

FIG. 1 shows an intraluminal filter 10 according to the invention, deployed within the lumen 12 of an artery 14. Filter 10 is shown downstream of an aneurysm 16 in the artery, the blood flow direction being indicated by arrow 18. Filter 10 is held on a tether 20 which leads to a catheter (not shown) allowing the filter to be retrieved from the lumen after a medical procedure repairing the aneurysm is completed.

Filter 10 comprises resilient monofilaments which preferably comprise braided wires 22. In the preferred embodiment wires 22 are co-braided with other filamentary members preferably comprising polymer yarns 24. The wires 22 and yarns 24 are braided into a generally bulbous or spherical shape. Wires 22 are braided in a relatively open mesh basket 26 and form a flexible structure supporting the polymer yarns which are braided to form a filter element 28 located distally and forming the downstream portion 30 of the filter 10. The wires 22 of the open mesh basket 26 are braided in a relatively open mesh and form an unobstructed upstream portion 32 of the filter to allow for unrestricted flow of blood or other fluid into the filter.

Wires 22 have diameters ranging from 5 to 500 microns. Nitinol, an alloy of nickel and titanium, is the preferred material for wires 22 because it is easily braided, biocompatible, radiopaque and highly elastic, having a yield strength on the order of 65,000 psi. Other metals such as stainless steel, titanium, elgiloy and alloys of gold, tantalum.or platinum having significant flexibility, elasticity, resilience and stiffness can also be used to form the wires. Non-metals such as polymers can also be used, but are not preferred for vascular applications because the filaments are not radiopaque and require larger diameters to achieve the strength and stiffness needed, resulting in a generally bulkier filter.

The properties of the wires in conjunction with the braided structure allow the filter to deform elastically and radially contract from the bulbous form, shown in FIG. 1, to the thin, elongated cylindrical shape, seen in FIG. 2a. These wire and braid characteristics allow the filter 10, when in its cylindrical shape, to be inserted into the lumen of a catheter and then to expand radially to the bulbous shape of FIG. 1 automatically when released from the catheter within the artery 14, as described in further detail below.

Filter element 28 (see FIG. 1), located distally and forming the downstream portion 30 of the filter 10, is preferably a braided polymer textile formed from polyester yarns 24 in a densely braided mesh 34 co-braided with the metal wires 22. Polyester is the preferred material because it is a well understood biomedical material with a long and successful implant history. Furthermore, polyester can be coated with bioactive chemicals, ablated or fused in a precisely controlled manner by heat, such as from a laser, which is useful for the manufacture of the filter as described below.

Other materials useful for forming the polymer yarns of the filter element 28 include ePTFE, PTFE, PET, nylon, polyethylene, PGA and PLA. The yarn material is chosen for its compatibility with human tissue, as well as mechanical properties, such as elongation, strength, flexibility and toughness.

Yarns 24 range in diameter from 5 microns to 500 microns (5 to 100 denier). Multifilament yarns are preferred, but other types of yarns such as monofilament yarns, textured or flat yarns, and yarns formed from slit film can also be used.

While a textile filter element is preferred, other filter means are also feasible, such as solid films with holes formed by chemical means, laser or mechanical penetration, to achieve the desired porosity.

The diameter of the polymer yarns 24 and the mesh density are controlled to yield a filter element 28 preferably having a porosity ranging between 60% and 90%. The porosity is quantified by the ratio of the area of openings in the fabric to the total fabric area, multiplied by 100. Mesh in this porosity range will capture emboli in the bloodstream yet allow blood to flow substantially unimpeded, thus, allowing the filter 10 to remain in place for relatively long durations without occluding the artery 14. This enables the filter to be used in lengthy medical procedures.

Intraluminal filters 10 according to the invention are preferably formed by co-braiding metal wires 22 and polymer yarns 24 together on a braiding machine into a continuous tube or sleeve. The differing mesh densities for the wires and the polymer yarns are effected by the ratio of carriers on the braiding machine having wire versus the carriers having polymer yarns. For example, to create the dense mesh 34 of polymer yarns 24 required for the filter element 28, between 24 and 196 carriers will feed polymer to the braiding machine, whereas the open mesh basket 26 of wires 22 requires between 24 and 48 carriers feeding wire to the braiding machine. A preferred braiding set up features 72 filaments of 40 denier polyester yarn, 12 filaments of 0.005 inch diameter nitinol wires interbraided over a 6 mm mandrel at a braid angle of 37°. This configuration achieves a porosity of 80%. In an alternate embodiment, 132 filaments of 20 denier polyester yarn are interbraided with 12 filaments of 0.005 inch diameter nitinol wires over a 6 mm mandrel at a braid angle of 37°, achieving a porosity of 78%. The porosity of the filter element is readily controlled by varying the denier of the yarn and the mesh density. These parameters also affect the relative flexibility of the filter element, with higher mesh densities yielding stiffer filters.

The braiding machine forms a continuous tube of co-braided metal wires and polymer yarns having an unstressed diameter "D" (see FIG. 1) which is tailored to be slightly larger than the particular lumen in which it will be used. A larger diameter tube ensures that the filter will be slightly compressed by the inner wall 36 of lumen 12 and have an interference fit within the lumen. Friction between the filter 10 and inner wall fixes the position of the filter when it is deployed within the lumen.

Figure 3:
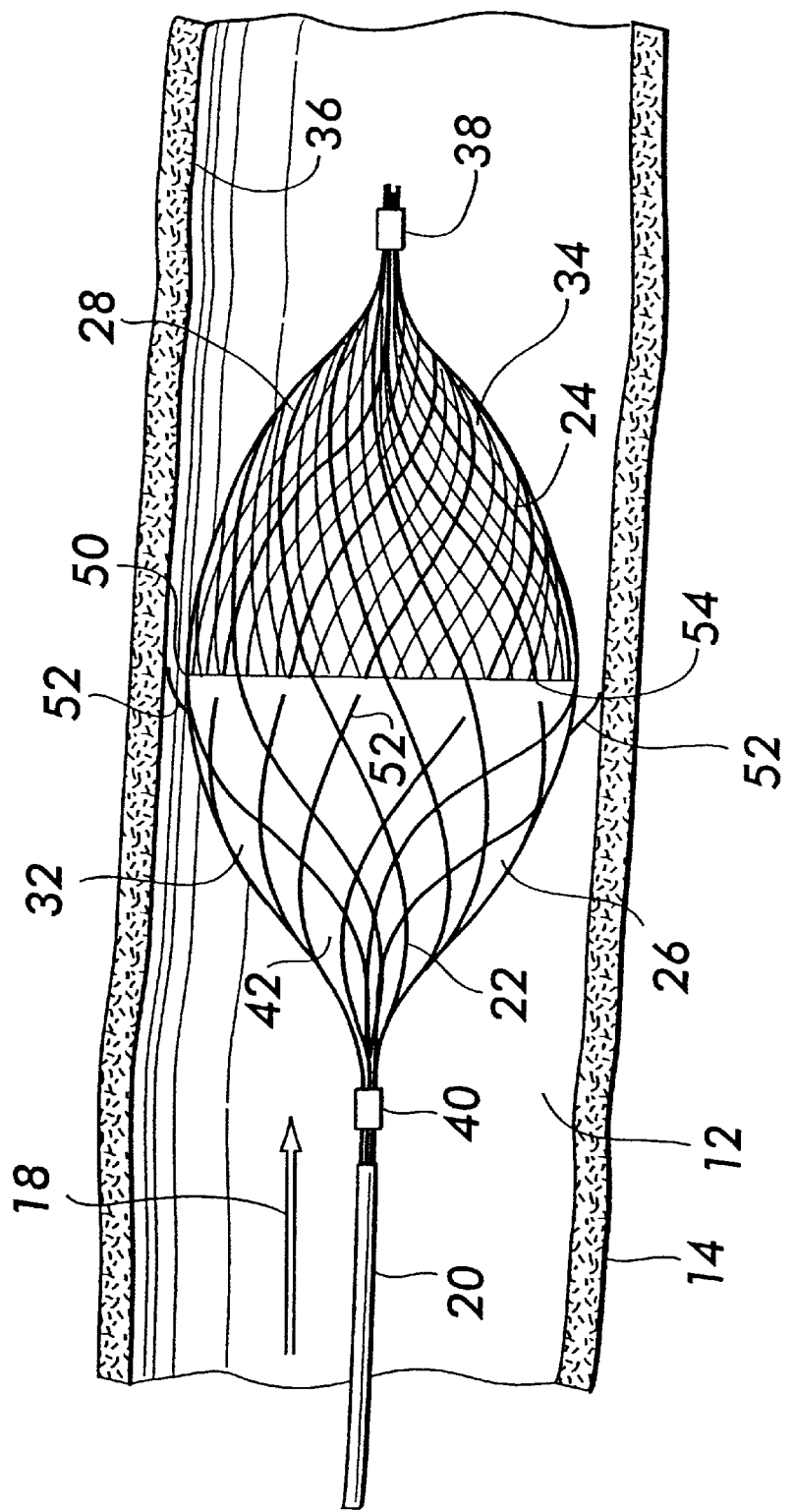
FIG. 3 shows a partial cross-sectional view of an alternate embodiment of an intraluminal filter as shown in FIG. 1.

In an alternate embodiment of the intraluminal filter, shown in FIG. 3, a plurality of the flexible wires 22 are cut at points 50 adjacent to the downstream portion of the basket 34 having the filter element 28. Cutting certain of the wires forms projections, in the form of the cut wire end portions 52, which extend angularly outwardly from the filter and point in the down stream direction. The end portions 52 engage the lumen inner wall 36 and prevent downstream motion of the filter. The cut wires are relatively unrestrained by the open mesh of the upstream portion 32 of the basket 26, allowing the end portions 52 to project outwardly. The complementary cut ends 54 residing on the downstream portion 30 of the filter are restrained by the filter element 28 and do not project outwardly. Because the end portions 52 point downstream they prevent downstream motion of the filter but do not hinder upstream filter motion. The end portions readily disengage from the lumen when the filter is moved upstream, as for example when the filter is being withdrawn from the lumen into the catheter for removal of the filter from the vascular system. Furthermore, because the cut wires are interbraided with uncut wires the end portions 52 as well as the complementary cut ends 54 retract readily into the smaller diameter cylindrical shape, allowing the filter 10 to be retracted back into the catheter as described below. In this embodiment, it is preferred to interbraid 24 wires to form the basket 26, and cut every other wire, spacing the 12 cut wires at 30° intervals circumferentially around the filter, and achieving a ratio of cut to uncut wires of one to one.

To form a filter 10, the continuous, co-braided tube is cut into discrete lengths "L" and cinched or crimped at each end by cinches 38 and 40. The length imparts stability to the filter against slippage and rotation when deployed in the lumen, and lengths on the order of 1.1 to 1.5 times the diameter of the lumen inner diameter are preferred for vascular use, for example. It is preferred to use a radiopaque, ductile material, such as platinum or stainless steel, to form cinches 38 and 40. Radiopaque material allows the filter to be detected via X-rays or fluroscopy to accurately determine its position.

Figure 4:
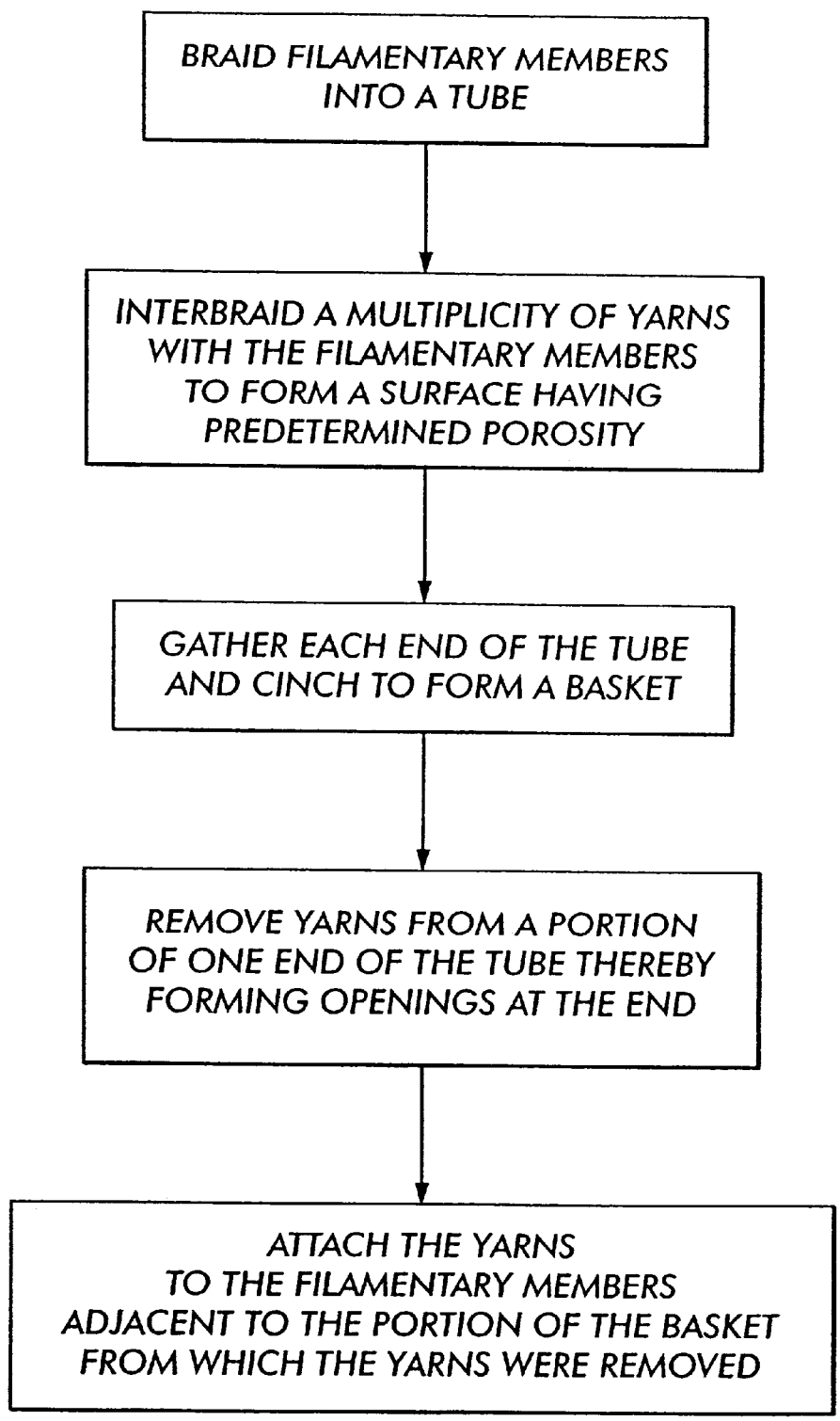
FIG. 4 shows a flow chart describing a method of making an intraluminal filter according to the invention.

Cinching the ends distorts the tube into the bulbous shape seen in FIG. 1. Polymer yarns initially extend in a dense mesh over the entire surface of the bulbous shape, and these yarns must be removed from the upstream portion 32 to expose the open mesh basket 26 of wires 22 and form the entrance openings 42 allowing blood or other fluid to flow into the filter. It is preferred to use a laser to ablate the polymer yarns off of the upstream portion, although other ablation methods, including chemical and mechanical methods, are feasible. The laser also fuses or heat seals the remaining polymer yarns 24 together and to the wires 22 at the boundary 31 between the upstream and downstream portions of the filter. The upstream cinch 40 forms a convenient point for attaching tether 20. FIG. 4 presents a flow chart which depicts the steps for forming a filter according to the invention.

Because filter 10 has a support structure of resilient, flexible wires 22 braided in an open mesh basket 26 it is possible to distort the filter from its nominal or unstressed bulbous shape into an elongated cylindrical shape, seen in FIG. 2a, by applying a tensile force to cinches 38 and 40. It is well known that braided structures exhibit a "trellis effect" wherein the braided wires rotate and slide relatively to one another when a force is applied. For the bulbous structure of the filter, this effect results in radial contraction of the filter with axial expansion and radial expansion upon axial contraction.

When the aforementioned tensile force is removed, the braid springs back into its nominal or unstressed shape due to elastic forces generated within the wires in response to the distortion. The degree of distortion per unit force applied is proportional to the mesh density with less dense meshes allowing for proportionally greater distortion from the nominal shape and higher associated elastic spring back forces.

These properties of braided structures are used to great advantage in the filter 10 according to the invention, as shown in the sequence of FIGS. 2a–2f, which illustrates the use of the filter to capture emboli dislodged while installing a stent graft to repair an aneurysm.

FIG. 2a depicts an artery 14 having an aneurysm 16. A catheter 44 containing filter 10 and a stent graft 46 is positioned with its tip 44a downstream of aneurysm 16 as indicated by arrow 18 showing the direction of blood flow. Filter 10 is nearer the tip 44a of the catheter as it will be deployed first. While within catheter 44, filter 10 is maintained in its distorted cylindrical shape by the restraint of the catheter wall, thus, the filter is able to slide along the catheter through lumen 48.

FIG. 2b shows filter 10 being pushed out from the tip 44a at the downstream location. As the filter emerges from the catheter 44, it is no longer restrained and springs open automatically by virtue of the elastic forces within the resilient wires 22. The filter tries to assume its stress free shape but encounters inner wall 36 of artery 14. The filter lodges against the inner wall 36 and friction between the filter and inner wall hold the filter in position despite the blood pressure which would otherwise tend to move the filter further downstream. Additionally or alternately, projections 52, when present, extend outwardly and engage the inner wall 36 (see FIG. 3) to prevent downstream motion of the filter.

FIG. 2c shows filter 10 fully deployed from the catheter in the proper orientation with the unobstructed upstream portion 32 of the open mesh basket 26 facing upstream and the dense mesh filter element 28 forming a concavity facing the blood flow 18. The porosity of the filter element 28 allows blood to flow without significant resistance. Catheter tip 44a is positioned at the downstream end 16a of aneurysm 16 in preparation to deploy the stent graft 46 to repair the aneurysm.

In FIG. 2d, the stent graft is shown partially deployed within artery lumen 12 and attaching itself to the inner wall 36 of artery 14. This procedure dislodges emboli 50 from the artery inner wall. The emboli become entrained with the blood and flow downstream, through the unobstructed upstream portion 32 of the open mesh basket 26 and into filter 10 where the emboli become entrapped against the dense mesh 34 of polymer yarns 24 forming the filter element 28 on the downstream portion 30 of the filter.

FIG. 2e shows the stent graft 46 fully deployed and installed at aneurysm 16, the repair procedure being complete and no further emboli being dislodged from the artery.

FIG. 2f shows filter 10 being recovered from artery 14. Recovery is effected by moving catheter tip 44a downstream into contact with upstream portion 32 of filter 10. Tension is applied to tether 20 to hold the filter in place as the catheter is pushed against the filter. Again, the flexible properties of the braided structure are manifest as filter 10 radially collapses as it is drawn into the catheter lumen 48 by the dual opposing action of the catheter and the tether. Blood in the filter flows out through filter element 28, but emboli 50 remain trapped within the filter and are removed from the artery once the filter is fully within the catheter and the catheter is removed from the artery.

Use of the intraluminal filter according to the invention will improve the success rate of vascular procedures by preventing complications due to embolisms caused by emboli dislodged during the procedure. Although the preferred field of application of the filter is for vascular applications, it can be employed in many procedures requiring that a temporary filter be deployed to collect, trap and separate particles from a fluid stream within a lumen.

What is claimed is:

1. An intraluminal filter positionble within a lumen for separating particles from a fluid flowing within said lumen, said intraluminal filter comprising:

a first plurality of filamentary members formed of a flexible, resilient material and interlaced in a relatively open mesh to form a basket, said first filamentary members elastically deforming said basket from a first shape state having a first diameter sized to allow said basket to slidingly fit within the bore of a catheter positionable within said lumen, to a second shape state having a second diameter substantially larger than said first diameter and sized to allow said basket to sealingly interfit within said lumen, said basket being biased by internal elastic forces within said first filamentary members to assume said second shape state when released from said catheter;

a second plurality of filamentary members interlaced with one another and with said first filamentary members to form a concave first portion of said basket, said basket having a second portion remaining unobstructed and arranged facing said concave first portion, said relatively open mesh having openings sized to allow said fluid and said particles to flow through said second portion into said concave first portion when said second portion is oriented upstream within said lumen, said concave first portion comprising a filter element having second openings of predetermined size smaller than the first named openings, said second openings being sized to capture entrained particles while allowing said fluid to flow therethrough.

2. An intraluminal filter according to claim 1, wherein said first filamentary members are braided into a tube having a predetermined length, said tube having oppositely arranged ends gathered and cinched to form said basket, one of said ends forming said second portion of said basket and being unobstructed to form said first openings.

3. An intraluminal filter according to claim 2, further comprising a flexible tether attached to said one end of said basket, said tether having a predetermined length and being extendable through said catheter for allowing said filter to be manually withdrawn from said lumen into said catheter bore.

4. An intraluminal filter according to claim 1, wherein said second filamentary members comprise a thermoplastic polymer.

5. An intraluminal filter according to claim 4, wherein said second filamentary members are heat sealed to said first filamentary members adjacent to said second portion of said basket.

6. An intraluminal filter according to claim 1, further comprising a plurality of projections extending outwardly from said filter and interengaging an internal surface of said lumen for fixing said filter at a predetermined location therein.

7. An intraluminal filter according to claim 6, wherein said projections comprise a third plurality of filamentary members interlaced with said first plurality, said filamentary members of said third plurality each having an end located adjacent to said first portion of said basket, each said end extending angularly outwardly of the filter and facing downstream to engage said lumen internal surface.

8. An intraluminal filter according to claim 7, wherein each said end is formed by cutting said filaments of said third plurality, said ends adjacent to said first portion of said basket being relatively unrestrained by said first plurality of filamentary members to allow said ends to project angularly outwardly, end portions at said second portion of said basket being restrained by said filter element.

9. An intraluminal filter for trapping and retaining particles entrained in a fluid flowing within a lumen, said filter comprising:

an elastically deformable basket formed of a plurality of flexible, resilient filamentary members interlaced in a relatively open mesh of a size allowing flow of said fluid and said particles therethrough, said basket being elastically radially compressible to a first shape state having a first predetermined diameter sized to slidingly interfit within a catheter positionable within said lumen, and being radially expandable to a second shape state having a second predetermined diameter larger than the first to sealingly interfit within said lumen, said basket being biased by elastic forces of said filamentary members to nominally assume said second shape state, and being elastically and repeatably deformable between said shape states;

said basket having a relatively open first portion and filter means disposed opposite to said first portion, said filter means having a concave surface of predetermined porosity facing said first portion for capturing said particles when said basket is in said second shape state and positioned in said lumen with said first portion arranged upstream of said filter means.

10. An intraluminal filter according to claim 9, wherein said filamentary members are monofilament wires.

11. An intraluminal filter according to claim 10, wherein said filamentary members are interlaced by braiding.

12. An intraluminal filter according to claim 11, wherein said filter means comprises a multiplicity of multifilament yarns braided with one another and with said filamentary members in a relatively closed mesh.

13. An intraluminal filter according to claim 12, wherein said yarns consist essentially of polyester.

14. An intraluminal filter according to claim 10, wherein said filamentary members comprise a radiopaque material.

15. An intraluminal filter according to claim 14, wherein said radiopaque material is nitinol.

16. An intraluminal filter according to claim 9, further comprising a flexible tether attached to said basket on said second portion, said tether being elongated and extendable through said catheter for manually drawing said basket into said catheter.

17. An intraluminal filter according to claim 9, wherein said lumen is a vascular lumen.

18. An intraluminal filter according to claim 9, wherein the porosity of said filter means ranges between about 60% and 90%.

19. An intraluminal filter according to claim 9, further comprising a plurality of projecting members having end portions projecting angularly outwardly from said filter and being interengagable with said lumen for preventing downstream movement of the filter, said end portions pointing in the downstream direction to allow said end portions to readily disengage from said lumen when said filter is moved in an upstream direction for retraction of the filter into the catheter.

20. An intraluminal filter according to claim 19, wherein said projecting members are monofilament wires being selected ones of said resilient filamentary members comprising said basket, said projecting members being present in the ration of about one to one with said resilient filamentary members.

21. A method of forming an intraluminal filter comprising the steps of:

braiding a plurality of flexible, resilient filamentary members into a relatively open mesh forming an elastically deformable tube, said filamentary members providing a radial bias to said tube, urging said tube to assume a predetermined length and diameter;

interbraiding a multiplicity of yarns with said first filamentary members to form with said filamentary members a surface having a predetermined porosity;

gathering each end of said tube and cinching each said end together to form an elastically deformable basket;

removing said yarns from a portion of said basket at one end of said tube thereby forming openings at said one end; and attaching said yarns to said first filamentary members adjacent to said portion of said basket.

22. A method of forming an intraluminal filter according to claim 21, wherein said yarns are formed of a polymer, said polymer having a lower melting point than said flexible, resilient filamentary members and said removing step is performed by ablating said yarns.

23. A method of forming an intraluminal filter according to claim 22, wherein said attaching step is performed by heat sealing said yarns to said filamentary members.

* * * * *